US00PP10213P

United States Patent [19]

Wain

[11] Patent Number: Plant 10,213

[45] Date of Patent: Jan. 27, 1998

[54] CHRYSANTHEMUM PLANT NAMED 'JENNY WREN'

[75] Inventor: Peter Wain, Portsmouth, United Kingdom

[73] Assignee: Cleangro Ltd., Chichester, United Kingdom

[21] Appl. No.: 733,727

[22] Filed: Oct. 18, 1996

[51] Int. Cl.[6] ..... A01H 5/00

[52] U.S. Cl. ..... Plt./76

[58] Field of Search ..... Plt./76, 82

*Primary Examiner*—Howard J. Locker

*Attorney, Agent, or Firm*—C. A. Whealy

[57] ABSTRACT

A distinct cultivar of Chrysanthemum plant named 'Jenny Wren', characterized by its vigorous and upright growth habit; numerous small leaves; decorative-type inflorescences; magenta-colored ray florets; numerous inflorescences per plant; and good garden performance.

2 Drawing Sheets

The present invention relates to a new and distinct cultivar of Chrysanthemum plant, botanically known as *Dendranthema gradiflora* and referred to by the cultivar name Jenny Wren.

The new cultivar is a product of a planned breeding program conducted by the inventor in Chichester, West Sussex, United Kingdom. The objective of the breeding program was to create new Chrysanthemum cultivars having desirable inflorescence colors and good garden performance.

The new cultivar originated from a cross made by the inventor of the cultivar Bravo (U.S. Plant Pat. No. 6,888) as the female, or seed, parent with the proprietary selection 7/GM/94 as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Jenny Wren'. These characteristics in combination distinguish 'Jenny Wren' as a new and distinct cultivar:

1. Vigorous and upright growth habit.
2. Numerous small leaves giving a bushy, dense appearance.
3. Decorative-type inflorescences.
4. Magenta-colored ray florets.
5. Numerous inflorescences per plant.
6. Good garden performance.

The cultivar Jenny Wren has not been observed under all possible environmental conditions. The phenotype may vary somewhat with variations in environment such as temperature, daylength and light intensity, without, however, any variance in genotype.

In side-by-side comparisons in Chichester, West Sussex, United Kingdom, under commercial practice, plants of the new Chrysanthemum are more compact and flower later than plants of the female parent, the Chrysanthemum cultivar Bravo. In the same comparisons, plants of the new Chrysanthemum are more compact, less vigorous and have more ray florets than the male parent, the proprietary selection 7/GM/94.

Plants of the new Chrysanthemum can be compared to the cultivar Sundoro (U.S. Plant Pat. No. 7,225). However, in side-by-side comparisons conducted in Oxnard, Calif., under commercial practice, plants of the new Chrysanthemum differed from plants of the cultivar Sundoro in the following characteristics:

1. Plants of the new Chrysanthemum are more vigorous and taller than plants of the cultivar Sundoro.
2. Plants of the new Chrysanthemum have more than twice as many leaves as plants of the cultivar Sundoro. Plants of the new Chrysanthemum appear denser than plants of the cultivar Sundoro.
3. Plants of the new Chrysanthemum have leaves that are less than half as large as leaves of plants of the cultivar Sundoro.
4. Plants of the new Chrysanthemum have more inflorescences and more ray florets than plants of the cultivar Sundoro.
5. Plants of the new Chrysanthemum have smaller inflorescences and smaller ray florets than plants of the cultivar Sundoro.
6. The abaxial surface of the ray florets of the new Chrysanthemum is light pink whereas the abaxial surface of the ray florets of the cultivar Sundoro is light orange.
7. Plants of the new Chrysanthemum have longer peduncles than plants of the cultivar Sundoro.

A detailed comparison of plants of the new Chrysanthemum and the cultivar Sundoro appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical flowering 16.5-cm container of 'Jenny Wren' with one cutting in the container.

The second photograph comprises a close-up view of five leaves at different stages of development and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18C, average day temperatures of 30C, and light levels of 2,000 (cloudy conditions) to 9,000 (sunny conditions) footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultiver Jenny Wren.

Commercial classification: Garden chrysanthemum.

Parentage:

*Female, or seed, parent.*—*Dendranthema grandiflora* cultivar Bravo (U.S. Plant Pat. No. 6,888).

*Male, or pollen, parent.*—*Dendranthema grandiflora* proprietary selection 7/GM/94.

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Vigorous and rapid growth rate. Stems upright, uniform habit and freely branching.

*Plant height.*—About 26 cm.

*Lateral branch length.*—About 23 cm.

*Quantity of lateral branches after removal of apical meristem.*—About 3.

*Stem color.*—147D.

*Foliage description.*—Number of leaves per plant: About 100. Number of leaves per lateral branch: About 34. Leaf arrangement: Alternate. Leaf size, fully expanded: Length: About 1.9 cm. Width: About 1.6 cm. Leaf apex: Rounded, slightly apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 2.5 cm. Color: Young foliage abaxial surface: 137A. Young foliage abaxial surface: 147B. Fully expanded foliage adaxial surface: 147A. Fully expanded foliage abaxial surface: 147B. Venation abaxial surface: 147C. Venation adaxial surface: 147C. Petiole: 147C.

Flowering description:

*Appearance.*—Decorative inflorescence form. Inflorescences borne on terminals above foliage, arising from leaf axils. Disc and ray florets arranged acropetally on a flat capitulum.

*Flowering response.*—Under natural conditions, plants flower in the autumn. At other times of the year, inflorescence initiation and development can be induced under short day/long night conditions (at least 13.5 hours of darkness). Plants exposed to about 4 weeks of long day/short night conditions after sticking followed by photoinductive short day/long night conditions, flower about 49 days later.

*Quantity of inflorescences.*—About 8 inflorescences per flowering stem.

*Inflorescence size.*—Diameter: About 4.3 cm. Depth (height): About 1.6 cm. Diameter of disc: About 3 mm.

*Opening inflorescences.*—Bud shape: Spherical. Bud size: Length: About 8 mm. Width: About 9 mm. Bud color: 58A.

*Ray florets.*—Shape: Strap-like, narrow. Size: Length: About 2 cm. Width: About 5 mm. Apex: Tri-dentate. Base: Acute. Margin: Entire. Texture: Matte, smooth and glabrous. Aspect: Flat. Number of ray florets per inflorescence: About 196. Color: When opening, adaxial surface: 58A. When opening, abaxial surface: 65D. Mature, adaxial surface: 58A. Mature, adaxial surface: 65C. Fading to: 67C.

*Disc florets.*—Shape: Tubular. Size: Length: About 4 mm. Width: About 1 mm. Number of disc florets per inflorescence: About 6. Color: Immature: 2D. Mature: 2D.

*Peduncle.*—Aspect: Strong and angled about 35 to 40° to the stem. Length: First peduncle: About 5.2 cm. Fourth peduncle: About 7.5 cm. Texture: Pubescent. Color: 138B.

*Reproductive organs.*—Androecium: Present on disc florets only. Anther color: 3A. Pollen: Moderate, 3A in color. Gynoecium: Present on both ray and disc florets. Style color: 154C.

Disease resistance: No known Chrysanthemum diseases observed to date on plants grown under commercial greenhouse conditions.

Seed production: Seed production has not been observed.

CHART A

| CHARACTERISTIC | 'JENNY WREN' | 'SUNDORO' |
|---|---|---|
| PLANT HEIGHT | About 26 cm | About 23 cm |
| LATERAL STEM LENGTH | About 23 cm | About 20 cm |
| GROWTH RATE | Rapid | Moderate |
| VIGOR | High | Moderate |
| QUANTITY OF LEAVES PER PLANT | About 100 | About 45 |
| QUANTITY OF LEAVES PER LATERAL BRANCH | About 34 | About 15 |
| LEAF LENGTH | About 1.9 cm | About 4.4 cm |
| LEAF WIDTH | About 1.6 cm | About 3.7 cm |
| YOUNG FOLIAGE, ADAXIAL | 137A | 147A |
| QUANTITY OF INFLORESCENCES PER LATERAL STEM | 8 | 6 |
| INFLORESCENCE DIAMETER | About 4.3 cm | About 5.6 cm |
| INFLORESCENCE DEPTH | About 1.6 cm | About 2 cm |
| BUD SHAPE | Spherical | Flattened |
| BUD COLOR | 58A | 70D |
| RAY FLORET SHAPE | Strap-like | Spatulate |
| RAY FLORET APEX | Tri-dentate | Emarginate with small notch |
| RAY FLORET LENGTH | About 2 cm | About 2.6 cm |
| RAY FLORET WIDTH | About 5 mm | About 8 mm |
| RAY FLORET COLOR, WHEN OPENING, ADAXIAL | 58A | 60C |
| RAY FLORET COLOR, WHEN OPENING, ABAXIAL | 65D | 36B |
| RAY FLORET COLOR, MATURE, ADAXIAL | 58A | 70B |
| RAY FLORET COLOR, MATURE, ABAXIAL | 65C | 27B |
| RAY FLORET COLOR FADING TO | 67C | 70C |
| NUMBER OF RAY FLORETS PER INFLORESCENCE | About 196 | About 150 |
| NUMBER OF DISC FLORETS PER INFLORESCENCE | About 6 | About 20 |
| DISC FLORET COLOR, IMMATURE | 2D | 154C |
| DISC FLORET COLOR, MATURE | 2D | 154C |
| DIAMETER OF DISC | About 3 mm | About 6 mm |
| PEDUNCLE LENGTH, FIRST | About 5.2 cm | About 3.2 cm |
| PEDUNCLE LENGTH, FOURTH | About 7.5 cm | About 5.4 cm |
| PEDUNCLE ANGLE TO STEM | About 35 to 40° | About 30° |

It is claimed:

1. A new and distinct cultivar of Chrysanthemum plant named 'Jenny Wren', as illustrated and described.

* * * * *

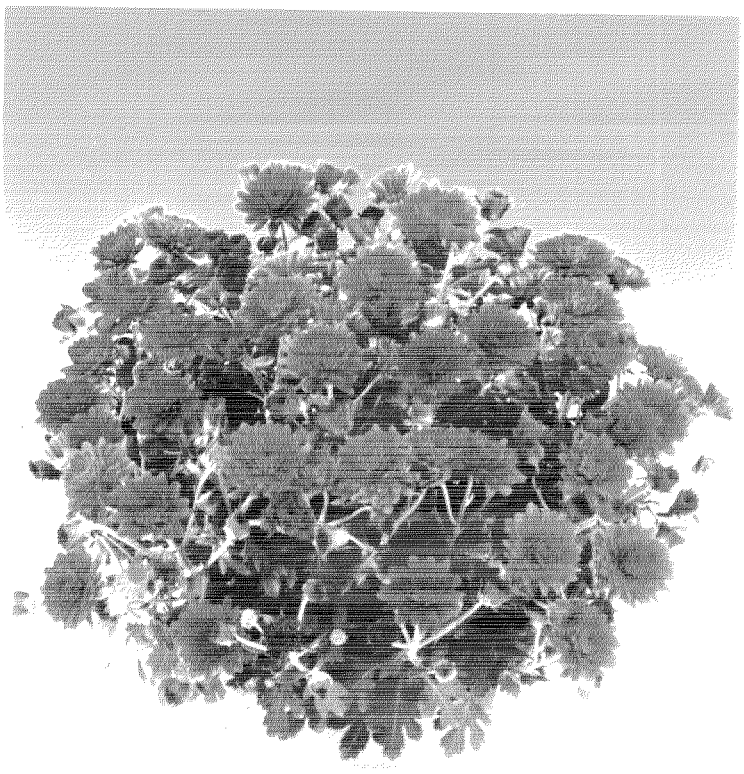

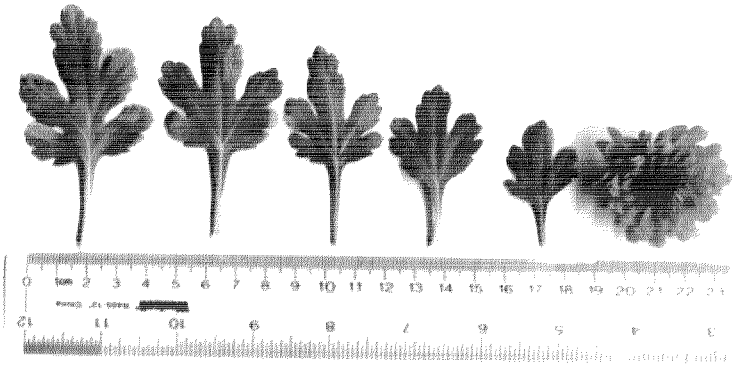

UNITED STATES PATENT AND TRADEMARK OFFICE

CERTIFICATE OF CORRECTION

PATENT NO. : Plant 10,213
DATED : January 27, 1998
INVENTOR(S) : Peter Wain

It is certified that error appears in the above-indentified patent and that said Letters Patent is hereby corrected as shown below:

Column 3, line 4, change "cultiver" to -- cultivar --.
Column 3, line 35, change "Young foliage abaxial surface: 137A." to --Young foliage adaxial surface: 137A. --.
Column 4, line 4, change "adaxial surface: 65C." to -- abaxial surface: 65C. --.

Signed and Sealed this
Tenth Day of August, 1999

*Attest:*

*Attesting Officer*

Q. TODD DICKINSON

*Acting Commissioner of Patents and Trademarks*